United States Patent [19]

Kufe

[11] Patent Number: 5,053,489

[45] Date of Patent: Oct. 1, 1991

[54] GENETICALLY ENGINEERED POLYPEPTIDES WITH DETERMINANTS OF THE HUMAN DF3 BREAST CARCINOMA-ASSOCIATED ANTIGEN

[75] Inventor: Donald W. Kufe, Wellesley, Mass.

[73] Assignee: Dana-Farber Cancer Institute, Inc., Mass.

[21] Appl. No.: 302,448

[22] Filed: Jan. 27, 1989

Related U.S. Application Data

[63] Continuation-in-part of Ser. No. 149,831, Jan. 29, 1988, Pat. No. 4,963,484.

[51] Int. Cl.$^5$ ................................................ C07K 7/00
[52] U.S. Cl. ...................... 530/350; 530/326; 530/324; 530/828; 530/836; 435/172.3; 435/69.1; 435/69.3; 935/9; 935/10; 935/38; 935/55
[58] Field of Search ............... 530/350, 326, 324, 333, 530/828, 832, 836; 435/7, 172.3, 68; 935/9, 10, 38, 55, 60; 536/27

[56] References Cited

PUBLICATIONS

S. Gendler et al, J. Biol. Chem., vol. 263, pp. 12820–12823 (Sep. 15, 1988 issue).
D. M. Swallow et al, Nature, vol. 327, 82–84 (1987).
S. J. Gendler et al, Proc. Natl. Acad. Sci., U.S.A., vol. 84, 6060 (1987).
S. J. Gendler et al, Abstract A-11, Biennial Intl. Breast Cancer Res. Conf., Miami (Mar. 1–5, 1987).
J. Siddiqui et al, Proc. Natl. Acad. Sci. (U.S.A.) vol. 85, pp. 2320–2323 (Apr. 1988).
Sekine et al, Journal of Immunology, vol. 135, No. 5, Nov. 1985, "Purification and Characterization of a High Molecular Weight Glycoprotein Detectable in Human Milk and Breast Carcinomas", pp. 3610–3615.

Primary Examiner—Christine Nucker
Assistant Examiner—Laurie A. Scheiner
Attorney, Agent, or Firm—Allan H. Fried

[57] ABSTRACT

A carbohydrate-free polypeptide coded for by a human DNA sequence of 309 nucleotides is immunologically reactive with monoclonal antibody against the human DF3 breast carcinoma-associated antigen. The nucleotide sequence is also useful as a probe to reveal restriction fragment length polymorphisms in human DNA.

7 Claims, 4 Drawing Sheets

FIG. 4

```
CGCACGGCTG GGGGGGCGGT GGAGCCCCGGG GCCGGCCTGC TCTCCGGGGC CGAGGTGACA    60
.CGTG...... C...C...... ..................................... 120
.................................G..G.......................  180
............G...G............................................. 240
.............................................................. 300
..............
```

GENETICALLY ENGINEERED POLYPEPTIDES WITH DETERMINANTS OF THE HUMAN DF3 BREAST CARCINOMA-ASSOCIATED ANTIGEN

This application is a continuation-in-part of application U.S. Ser. No. 149,831 filed Jan. 29, 1988.

BACKGROUND AND OVERVIEW OF THE INVENTION

Women with breast carcinoma tend to have elevated serum levels of a molecular antigenic determinant referred to as the DF3 antigen (DF3). This provides the basis for a currently used diagnostic assay in which samples of a women's serum are reacted with antibodies that bind specifically to DF3 (anti-DF3 antibodies; D. F. Hayes et al, *J. Clin. Oncol.* 4, 1542–1550; D. F. Hayes et al, *J. Clin. Invest.* 75, 1671–1678, 1985). The current invention relates to genetically engineered molecules that carry an immunologically active portion of the DF3 antigen; i.e., one that reacts with anti-DF3 antibodies. The molecules can be used to improve the reproducibility of the diagnostic assay. They can also be used as the basis for an alternative, more sensitive assay. In a related invention, individual women can be categorized as to their genetic material that determines the structure of DF3.

It has been demonstrated that naturally occurring DF3, that occurring in human breast carcinoma cells or the plasma of patients with breast cancer, is a member of a family of related but not identical high-molecular weight tumor-associated antigens (M. Abe et al, *J. Immunol.* 139, 257–261, 1987). Naturally occurring DF3 has been partially characterized as a high molecular weight mucin-like glycoprotein (H. Sekine et al., *J. Immunol* 135, 3610–3615, 1985; M. Abe et al., *J. Cell Physiol.* 126, 126–132, 1986), a molecule with both a polypeptide component and a carbohydrate component. The polypeptide component is comprised of one or more chains, each consisting of amino acids linked end-to-end in a specific sequence. On the average, it accounts for about 15 percent of the DF3 molecule, there being batch-to-batch variability and, within each batch, molecule-to-molecule variability, in the ratio of polypeptide to carbohydrate. As a result DF3 antigen is a collection of closely related but not necessarily identical molecules having the common property that they react with anti-DF3 antibodies. In human MCF-7 breast carcinoma cells, the antigen consists of two distinct glycoproteins with molecular weights in the range of 330 and 450 kilodaltons (kd), respectively (H. Sekine et al., *J. Immunol* 135, 3610–3615, 1985; M. Abe et al., *J. Cell Physiol.* 126, 126–132, 1986). DF3 antigen that circulates in the plasma of patients with breast cancer also has molecular weights ranging from approximately 300 to 450 kd (D. Hayes et al *J. Clin. Invest.* 75, 1671–1678, 1985).

In the currently used diagnostic assay for DF3, interpretation of the results requires that controls involving known amounts of DF3 be run. DF3 isolated from extracts of carcinoma cells is used to calibrate the assay. However, because of the above noted variability in the structure of DF3 antigen from molecule to molecule and from batch to batch, it would be advantageous to have a method of preparing a more reproducible version of the antigen. Improved reproducibility would be achieved if a carbohydrate-free polypeptide, capable of reacting with anti-DF3 antibody could be prepared. Previous work with the naturally occurring version had suggested that the carbohydrate portion of DF3 was essential for reaction with the anti-DF3 antibody. Nevertheless, in the current invention, synthesis of carbohydrate-free polypeptides with an antigenic determinant capable of reacting with anti-DF3 antibody (DF3 polypeptides), was achieved. Furthermore, these DF3 polypeptides can be synthesized in bacteria, which are expected to provide a less costly means of producing it.

The ability to synthesize an antigenically active polypeptide in bacteria also provides the basis for an alternative, potentially superior, means of detecting DF3 in human sera. In bacteria, the polypeptide can be synthesized with a higher specific radioactivity than is possible in human cells. It can then be used in a competition assay, one where anti-DF3 antibodies are allowed to react with a mixture of radioactive DF3 polypeptide that was synthesized in bacteria and nonradioactive antigen from the person's serum. This type of assay has been used with the carcinoembryonic antigen (CEA; See, for example, February, 1983 package insert for Carcinoembryonic Antigen Radioimmunoassay, Roche Diagnostics, Nutley, New Jersey 07110) the nonradioactive antigen will compete with the radioactive DF3 for antibody binding sites, the diminished binding of radioactivity being an index of the amount of DF3 antigen in the person's serum. This type of assay is expected to be able to detect smaller amounts of antigen in a person's serum than the currently used assay can.

In an example of the invention, a DF3 polypeptide was synthesized in the prokaryotic organism, *Escherichia coil (E. coli)*, a bacterium. Although there is still uncertainty as to both the number of polypeptide chains in a naturally occurring DF3 antigen molecule and the size of each chain, it is likely that the synthetic DF3 polypeptide represented less than a complete naturally occurring chain. Incomplete synthesis of an antigen polypeptide chain is a possible result of the procedure used to initially isolate DNA coding for an antigenically active site. First, messenger RNA (mRNA) was isolated from human breast carcinoma cells, which are known to synthesize the antigen. DNA copies of the mRNA were then made. (Failure to isolate intact mRNA molecules or synthesize complete DNA copies are two possible reasons why incomplete synthesis of an antigen chain is ultimately achieved.) Each DNA fragment was then attached to the DNA of a bacterial virus such that, if the fragment contained the ability to direct the synthesis of human DF3 polypeptide, that peptide would be expressed as part of a fused polypeptdie also containing the bacterial polypeptide, beta galactosidase. The resulting population of DNA molecules are distributed among a very large number of bacterial cells by a transfection process. At a subsequent step, each bacterial cell was tested for the ability to direct the synthesis of a polypeptide that would react with anti-DF3 antibody. Prior to completing the test, there was uncertainty as to whether the procedure employed would be successful in generating bacteria capable of making an antigenically active polypeptide: Not only would the polypeptide lack the carbohydrate portion it has in humans, there was an excellent chance that it would be smaller than its intact human form. As it turned out, several bacteria that produced antigenically active polypeptide were found, the one presented in detail here being typical of the group.

Regardless of the precise relationship of the *E. coli*-produced DF3 polypeptide to the naturally occurring one, the results presented above provide the following picture:

(1) the polypeptide component of DF3 has antigenic activity in the absence of any carbohydrate component;

(2) probably only a portion of the polypeptide (not more than 103 amino acids) is required for antigenic activity; and (3) the antigenically active portion of the DF3 polypeptide retains its antigenic activity when part of a polypeptide that is partly comprised of polypeptide sequences naturally foreign to it. As to this latter point, consider the fact that, in *E. coli*, the DF3 polypeptide was joined to the 116,000 dalton bacterial polypeptide, beta galactosidase. An advantage of this latter property is that the antigenically active site can be made part of a tyrosine-rich polypeptide, and radioactive iodine can be attached to the tyrosine residues, thereby increasing the specific radioactivity of the antigenic probe for use in the competition diagnostic assay.

Electrophoretic mobility patterns of an antigen are a reflection of its structure. The electrophoretic mobility patterns for circulating DF3 antigen are heterogeneous and differ among individuals (D. Hayes et al., *J. Clin. Invest.* 75, 1671–1678, 1985). Subsequent studies in family members have demonstrated that the electrophoretic mobility pattern of plasma DF3 antigen is genetically determined by codominant expression of multiple alleles at a single locus (D. Hayes et al., *Blood*, 1988, 71:436).

The aforementioned electrophoretic and genetic studies would not, however, make it obvious how one could detect the changes in DNA strucuture. Person-to-person variation in DNA structure of specific genes has been successfully demonstrated for some other genes using the technique of restriction fragment length polymorphism (RFLP). In RFLP analysis, one analyzes the size of DNA fragments that carry a particular gene after controlled digestion (by a restriction endonuclease) of that person's DNA. The technique can be used to categorize individuals genetically and also assist in identifying the individual who is the source of a particular tissue or group of body cells. Applicant used RFLP analysis to investigate the size of DNA fragments that carry the gene for the 103-amino acid antigenically active DF3 polypeptide. He discovered that indeed such RFLP analysis reveals variations in DNA structure that correlated with the variations in size of the circulating antigens. Whether there is a correction between a particular DNA structure and a predisposition to breast cancer is unknown.

SUMMARY OF THE INVENTION

In one aspect, the invention is a polypeptide that:

(1) is free or substantially free of bound carbohydrate; and (2) includes all or a portion of the amino acid sequence that is coded for by the human nucleotide sequence of

```
CGCACGGCTG GGGGGGCGGT GGAGCCCGGG
GCCGGCCTGC TCTCCGGGGC CGAGGTGACA    60
. CGTG. . . . . C. . . C. . . . . . . . . . . . . . . .
. . . . . . . . . . . . . . . . . . . . . . . . . . . . . . .  120
. . . . . . . . . . . . . . . . . . . . . . . . . . . . . . .
. . . . . . . . G . G. . . . . . . . . . . . . . . . . . .  180
. . . . . . . . . . . G. . . G. . . . . . . . . . . . . . .
. . . . . . . . . . . . . . . . . . . . . . . . . . . . . . .  240
. . . . . . . . . . . . . . . . . . . . . . . . . . . . . . .
. . . . . . . . . . . . . . . . . . . . . . . . . . . . . . .  300
```

-continued

. . . . . . . . .

a dot indicating that the nucleotide is identical to the one directly above it in the mode of representation used here; in a related aspect, the polypeptide includes all or a portion of one of the following four amino acid sequences:

1) ALA PRO GLU SER ARG PRO ALA PRO GLY SER THR ALA PRO PRO ALA HIS GLY VAL THR SER, or

2) ALA PRO ASP THR ARG PRO ALA PRO GLY SER THR ALA PRO PRO ALA HIS GLY VAL THR SER, or

3) ALA PRO GLU THR ARG PRO ALA PRO GLY SER THR ALA PRO PRO ALA HIS GLY VAL THR SER, or

4) ALA PRO ASP SER ARG PRO ALA PRO GLY SER THR ALA PRO PRO ALA HIG GLY VAL THR SER where each line of a sequence is read from left to right; of course, both an end-to-end linkage of any two of the amino acid sequences or an end-to-end linkage of two copies of any one of the sequences can be used in the polypeptide.

In another aspect, the invention is an antigen that reacts with anti-DF3 antibody and whose polypeptide component wash synthesized in a non-human cell under the direction of a human nucleotide sequence.

In another aspect, the invention is a recombinant DNA molecule that codes for a polypeptide capable of reacting with an anti-DF3 antibody; in another aspect, the invention is a prokaryotic organism containing such a recombinant DNA molecule in a form in which it can be expressed to direct the synthesis of a polypeptide that reacts with an anti-DF3 antibody. [A recombinant DNA molecule, in the present application, is one which does not occur in nature until human intervention leads to its construction and which, except for a specific desired nucleotide sequence, is free or substantially free of human DNA.]

In another aspect, the invention is a DNA molecule containing the sequence of 309 nucleotides depicted above, said DNA molecule being substantially free of other mammalian DNA.

In another aspect, the invention is a process of hybridizing a DNA molecule comprising the sequence of 309 nucleotides depicted above against restriction enzyme generated fragments of human DNA that have been fractionated on the basis of size. In another aspect, the invention is a process which comprises binding an anti-DF3 antibody to a polypeptide which was synthesized in a non-human cell under the direction of a human nucleotide sequence. In a further related aspect, it is a process which comprises binding an antibody to a polypeptide that was synthesized in a nonhuman cell said polypeptide being one that contains all or part of one of the following four amino acid sequences:

1) ALA PRO GLY SER ARG PRO ALA PRO GLY SER THR ALA PRO PRO ALA HIS GLY VAL THR SER, or

2) ALA PRO ASP THR ARG PRO ALA PRO GLY SER THR ALA PRO PRO ALA HIS GLY VAL THR SER, or

3) ALA PRO GLU THR ARG PRO ALA PRO GLY SER THR ALA PRO PRO ALA HIS GLY VAL THR SER, or

4) ALA PRO ASP SER ARG PRO ALA PRO GLY SER THR ALA PRO PRO ALA HIS GLY VAL THR SER.

In subgeneric aspects of the above inventions that involve DF3 polypeptides, the entire polypeptide sequence coded for by the human DNA component of pDF3.9 are required and, in other subgeneric aspects, those are the only naturally occurring DF3 sequences present.

In additional subgeneric aspects of the above inventions that involve anti-DF3 antibodies, the anti-DF3 antibody of the invention is that produced by hybridoma No. DF3 of the laboratory of Donald W. Kufe, Dana-Farber Cancer Institute, Boston, Mass. (Hybridoma No. DF3 ).

BRIEF DESCRIPTION OF THE DRAWINGS

FIG. 4: Nucleotide sequence of the pDF9.3 cDNA insert.

DETAILED DESCRIPTION

Library Screening

Figure 1:
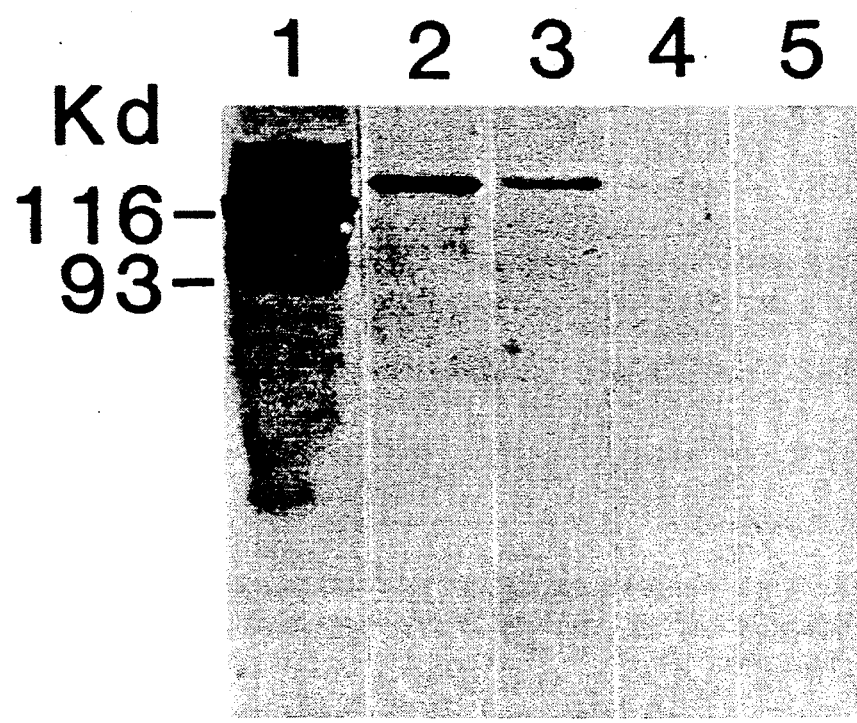
FIG. 1: Immunological identification of pDF9.3 encoded recombinant antigen. Lambda gt11 and pDF9.3 recombinant phage were used to lysogenize E. coli Y1089. Protein extracts were prepared from the lysogens and 10 μl of the bacterial lysates were electrophoresed in SDS/7.5% polyacrylamide gels, electroblotted onto nitorcellulose and, after the nitrocellulose was blocked with 1% BSA in Tris-buffered saline plus Tween 20, it was incubated with anti-beta-galactosidase antibody (Lane 1) or MAb DF3 (Lane 2). MAb DF3 was also preincubated with 10 ng (Lane 3), 100 ng (Lane 4) and 500 ng (Lane 5) of purified DF3 antigen prior to probing the filters. Antibody binding was detected by an enzyme linked immunoabsorbant assay (the antibody was reacted with goat anti-mouse IgG linked to alkaline phosphates) using nitroblue tetrazolium as substrate and developed with 5-bromo-4-chloro-3-nitryl phosphate (Reagents were those of the Protoblot Lambda gt11 Immunoscreening System, Promega Biotec, Madison, Wis.). Several apparent proteolytic breakdown products are noted using the anti-beta-galactosidase antibody.

An oligo (dT) primed cDNA library was prepared from human MCF-7 breast carcinoma cells in lambda gt11 (P. Walter et al., Proc. Natl. Acad. Sci., USA 82, 7889-7893. 1985). Immunologic screening of the lambda gt11 library was performed as previously described (R. A. Young et al., Proc. Natl. Acad. Sci., U.S.A. 80: 1194-1198, 1983) using affinity purified MAb DF3 (0.25 μg/ml) [D. Kufe et al., Hybridoma 3, 223-232, 1984, describes the isolation of the hybridoma, presently referred to as Hybridoma No. DF3 in the laboratory of Donald W. Kufe, Dana-Farber Cancer Institute, Boston, Mass. The hybridoma was injected into mice, the ascites recovered, and the Mab DF3 antibodies purified by the MAPS II kit of Biorad, Richmond, Calif.] and anti-mouse IgG conjugated with alkaline phosphates (Promega Biotech, Madison, Wis.). Positive plaques were isolated and the phage was further purified to homogeneity by repeated antibody screening. DNA was isolated from MAb DF3 positive recombinant phage, digested with EcoRI and electrophoresed in 1.2% agarose gels containing ethidium bromide to determine the size of the insert.

Analysis of Lysogens for Fusion Protein

Lysogenization of E. coli Y1089 with phage and induction of fusion protein with isopropyl-beta-D-thiogalactoside (IPTG) were performed as described previously (R. A. Young et al., Proc. Natl. Acad. Sci., U.S.A. 80: 1194-1198, 1983, R. A. Young et al., Science 222: 778-782, 1983). The lysate of IPTG induced lysogen was subjected to electrophoresis in SDS/7.5% polyacrylamide gels (U. K. Laemmli, Nature 227, 680-685, 1970) and transferred to nitrocellulose filters for immunoscreening (W. N. Burnette, Anal. Biochem. 112: 195-203).

Southern and Northern Blot Analyses

The human breast carcinoma cell lines (BT-20, T47D, MCF-7, ZR-75-1), an ovarian carcinoma cell line (OV-D) and the HL-60 promyeloctyic leukemia cell line were maintained in exponential phase (M. Abe et al., J. Immunol. 139: 257-261, 1987; E. Friedman et al., Cancer Res. 46, 5189-5194, 1986; E. Sariban et al, Nature 316, 64-66, 1985). BT-20 is ATCC No. HTB, 19, T47D is ATCC NO. HTB 133, MCF-7 is ATCC No. HTB 22, ZR-75-1 is ATCC No. ATC CRL 1500, and HL-60 is ATCC No. ATC CCL 240 at the American Type Culture Collection, Rockville, Md. High molecular weight DNA and total cellular RNA were isolated by the guanidine isothiocyanate/cesium chloride method (L. G. Davis et al., Basic Methods in Molecular Biology, Elseview, N.Y., p. 130-135, 1986). The DNA was digested with EcoRI, PstI or HindIII. The DNA fragments were separated by electrophoresis in 0.6% agarose gels and then transferred to nylong membranes. The prehybridization and hybridization conditions were as described in the Zeta Probe manual (Bio-Rad Laboratories, Richmond, Calif.). The purified RNA (20 μg) was analyzed by electrophoresis in 1% agarose-formaldehyde gels followed by transfer to nitrocellulose paper. The hybridization conditions were as described previously (E. Sariban et al., Nature, 316, 64-66, 1985). The pDF9.3 cDNA probe was labeled with [$^{32}$P] dCTP (Amersham, Arlington Heights, Ill.) by the random primer method (A. P. Beinburg et al., Anal. Biochem. 132, 6-13, 1984) to a specific activity of approximately $10^9$cpm/μg DNA.

Immunoblot Analysis

Cells were suspended in phosphate buffered saline (PBS) (pH 7.4), 0.2 mM phenylmethylsulfonyl fluoride and aprotinin (0.015 tryspin inhibitor units/ml). the suspensions were sonicated and protein concentration was determined by the Bio-Rad protein assay (Bio-Rad Laboratories). The protein samples (100 μg) were analyzed by electrophoresis in SDS/3–15% gradient polyacrylamide gels and transferred to nitrocellulose paper (H. Towbin et al., *Proc. Natl. Acad. Sci. USA* 76: 4350–4354 1979). The nitrocellulose filters were washed with 5% bovine serum albumin in PBS for 1h at room temperature (25° C.), incubated with MAb DF3 (0.25 μg/ml) for 2h, rabbit anti-mouse Ig for 1h and then $^{125}$I-labeled protein A for 2h. The filters were washed five times, dried and exposed to x-ray film.

Nucleotide Sequence Analysis

The 309 bp pDF9.3 cDNA insert was subcloned into the EcoRI site of *E. coli* phage M13mp8 and M23mp9. The DNA sequence was determined by sequencing both strands via the dideoxy chain termination method (F. Sanger et al., *Proc. Natl. Acad. Sci. U.S.A.* 74, 5463–5467, 1987) using Klenow fragment DNA polymerase I (New England Biolabs, Beverly, Mass.) and [alpha-$^{35}$S]dCTP (Amersham).

EXAMPLES

Isolation and characterization of cDNA clones coding for DF3 antigen

MAb DF3 was used to screen the lambda gt11 library prepared from MCF-7 cells. Screening of 800,000 plaques yielded three positive clones which were further purified by repeated antibody screenings. Physical mapping showed that each of these recombinant clones contained inserts of similar size and that they had similar restriction maps (data not shown). One clone, designated pDF9.3 was characterized further. A beta-galactosidase fusion protein was prepared by infecting *E. coli* Y1089 with pDF9.3 and then analyzed by immunoblotting. The lambda gt11 lysogen produced a protein corresponding in molecular weight and antigenicity to beta-galactosidase (FIG. 1, Lane 1). MAB DF3 was unreactive with beta-galactosidase and other antigens present in the bacterial lysate (data not shown). In contrast, the recombinant pDF9.3 lysogen produced a fusion protein with an estimated mass of 126 kd which reacted with both MAb DF3 (FIG. 1, Lane 2) and the anti-beta-galactosidase antibody (data not shown).

Competition assays were also performed to further confirm that the epitope expressed by pDF9.3 shares homology with that identified by MAb DF3 on the DF3 glycoprotein. Thus, MAb DF3 was preincubated with purified DF3 antigen (M. Abe et al., *J. Immonol.* 139: 257–261, 1987) before immunoblot analysis of the pDF9.3 fusion protein. Preincubation of MAb DF3 with increasing amounts of purified DF3 antigen progressively inhibited reactivity of the antibody with the fusion protein (FIG. 1, Lanes 3–5). This finding indicates that the epitope on the fusion protein originates from the same reading frame that codes for the DF3 epitope.

Southern Blot Analysis of Genomic DNA

Figure 2A:
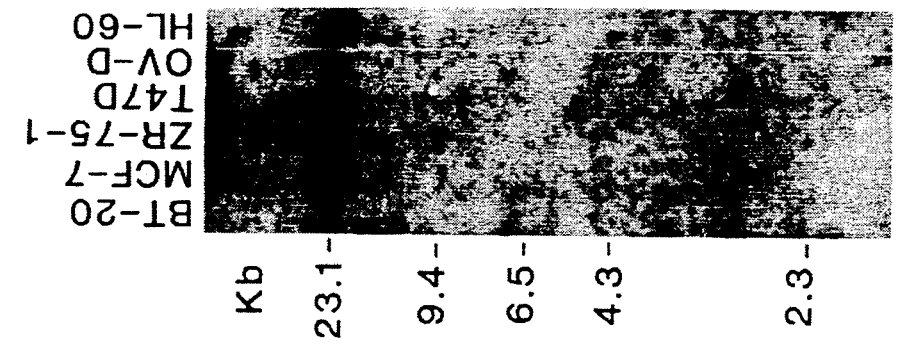
FIG. 2: Southern blot analysis of genomic DNA with the pDF9.3 probe. DNAs (20 μg) from human tumor cell lines were digested to completion with EcoRI (A), PstI (B) and HindIII (C), and electrophoresed in 0.6% agarose gels. The gels were denatured and the DNA fragments transferred to nylong filters. The filters were hybridized with the $^{32}$P-labeled pDF9.3 cDNA insert. The filters were then washed and exposed to x-ray film.
Figure 2B:
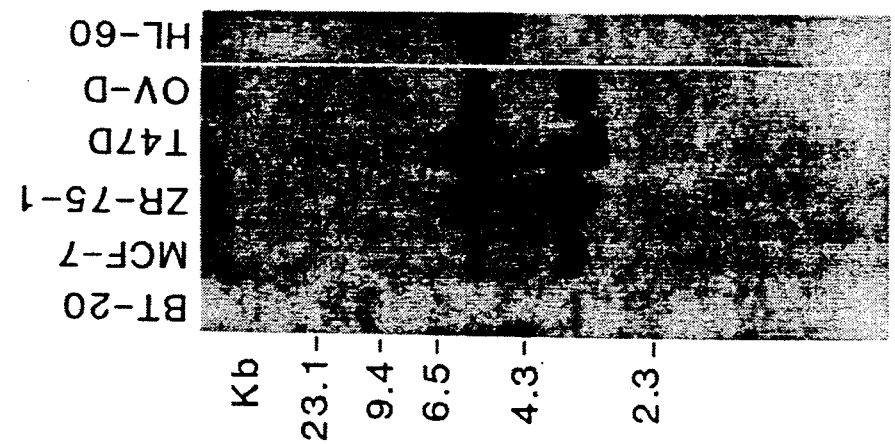
Figure 2C:
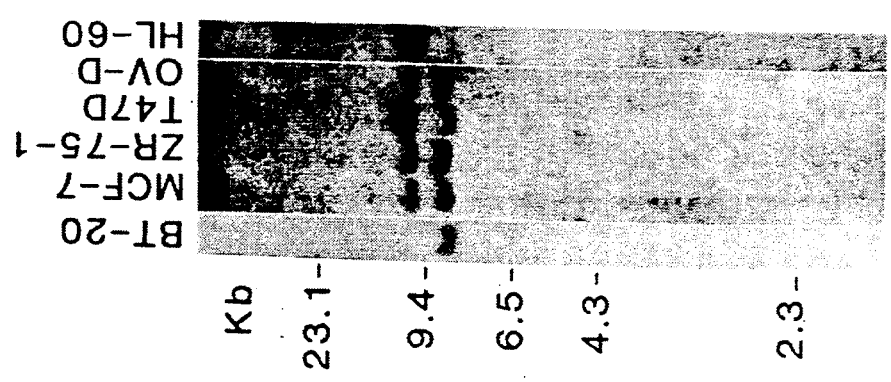

Identification of the cDNA was further studied by Southern blot hybridizations using $^{32}$P-labeled pDF9.3 prepared by subcloning the 309 bp insert into the EcoRI site of pUC8. Southern blot analysis of gemonic DNAs from the human tumor cell lines digested with EcoRI, PstI and HindIII are shown in FIG. 2. Hybridization of the 309 bp cDNA with the EcoRI and PstI DNA digest revealed restriction fragment length polymorphisms. The EcoRI digest yielded two fragments ranging from 7 to 12 kb in size for DNAs from each of the cell lines except BT-20. [In FIG. 2b, for BT-20, a faint band migrated the same distance as the approximately 3.0 kb band from MCF-7 cells.] Similar findings were obtained with the PstI fragments which ranged in size from 3.5 to 6 kb. The single EcoRI and PstI restriction fragments obtained with BT-20 DNA indicates the presence of two alleles of identical size or only a single allele. In contrast to these results, digestion of each of the DNA preparations with HindIII revealed only a single fragment of 23 kb. This finding would correspond to the absence of a HindIII restriction site in the alleles identified by pDF9.3.

Northern and Western Blot Analysis of DF3 Expression

Figure 3A:
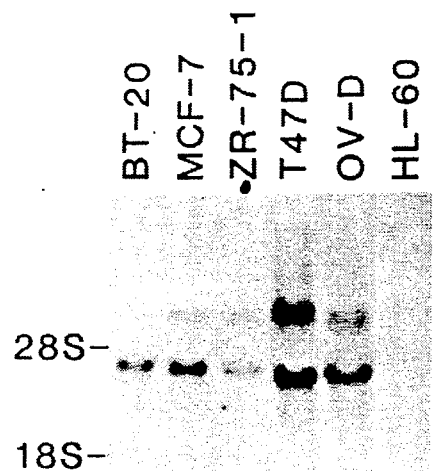
FIG. 3: Northern blot analysis with pDF9.3 and immunoblotting with MAb DF3. A. Total cellular RNA (20 μg) from human tumor cell lines was electrophoresed in a 1% agarose/formaldehyde gel, transferred to nitrocellulose and hybridized with the $^{32}$P-labeled pDF9.3 cDNA insert. B. Extracts of the human tumor cells were analyzed by SDS/3-15% polyacrylamide gel electrophoresis, immunoblotted with MAb DF3, and then reacted with rabbit anti-mouse Ig and $^{125}$I-labeled protein A.

Total cellulor RNA was prepared from each of the human tumor cell lines and monitored by Northern analysis for transcripts which hybridized to the pDF9.3 probe. A single 4.7 kb mRNA was detectable in BT-20 cells (FIG. 3A). In contrast, cell lines derived from the other breast and ovarian carcinomas expressed two transcripts which ranged in size from approximately 4.1 to 7.1 kb (FIG. 3A). Furthermore, no hybridization was detectable with RNA from HL-60 cells (FIG. 3A).

Figure 3B:
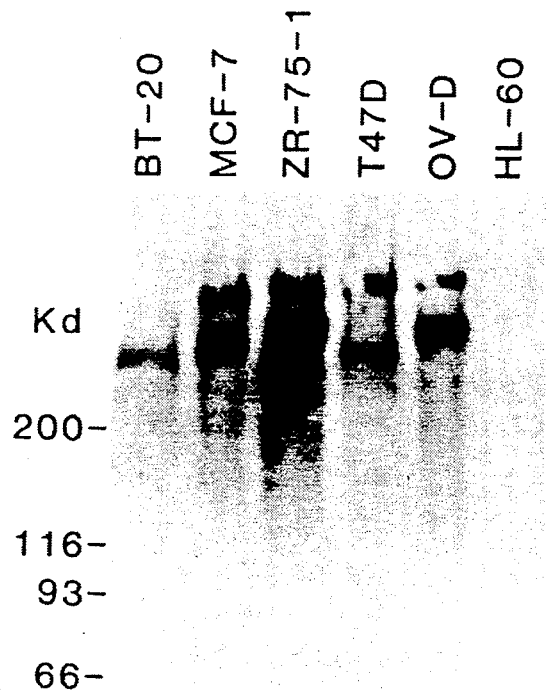

These findings by Northern blot analysis were compared to those obtained by immunoblotting with MAb DF3 and extracts prepared from each of the cell lines. The results indicated concordance in patterns of expression at the RNA and protein levels (FIG. 3B). Thus, BT-20 cells expressed a single transcript and a single DF3 glycoprotein, while the other epithelial cell lines expressed two transcripts and two DF3 antigens. Moreover, HL-60 cells had no detectable RNA and no detectable MAb DF3 reactive species. These findings further suggested that the transcripts detected by Northern analysis code for the DF3 core protein and that the size of these transcripts determines the size of the MAb DF3 reactive glycoproteins.

Nucleotide Sequence of pDF9.3

The reactivity of the fusion protein with MAb DF3 indicated that the cDNA insert contained an open reading frame which encodes for the DF3 epitope. The nucleotide sequence of pDF9.3 was found to be highly rich (85%) in GC base pairs (FIG. 4). Moreover, the sequence was found to consist entirely of 60 bp tandem repeats. These repeats were nearly identical with the exception of some transversions (FIG. 4). Furthermore, comparison of the pDF9.3 sequences with that of all genese with known sequences failed to reveal any significant homology.

Other Systems for the Invention

Prokaryotic organisms, especially bacteria, are preferred organisms for expressing the DF3 polypeptide. Many bacterial expression systems are well documented.

Techniques for taking a DNA sequence of known nucleotide sequence, such as pDF9.3, and inserting it into a plasmid or other DNA molecule so that its expression can be achieved, and preferably regulated, are well established.

Techniques for allowing an antibody to react with an antigen are well documented.

Expression of an Amino Acid Sequence from pDF9.3

Insertion of pDF9.3 into a plasmid can result in the expression of any one of six amino acid sequences, depending on which of its two DNA strands is in the same strand as the controlling plasmid promoter and depending upon which of the three possible reading frames for pDF9.3 is in phase with the initiation codon for the polypeptide that is fused to the pDF9.3-coded polypeptide. Northern blot analyses, done using RNA with sequences contained in one strand of pDF9.3 and then using RNA with sequences from the complementary pDF9.3 strand, and using RNA from BT-20 cells containing pDF9.3, demonstrated that the RNA strand depicted in FIG. 4 is the one which is transcribed into the RNA that is translated into the DF3 polypeptide. Furthermore, polypeptides that reacted with anti-DF3 antibody were detected in about half of E. coli cells that were infected with lambda gt11 phage containing, at its EcoRI site, pDF9.3 cDNA. As a result, based on known base sequences of lamba gt11, it was deduced that pDF9.3 DNA codes for a polypeptide that is capable of reacting with anti-DF3 antibody and that contains the following four closely related amino acid sequences:

1) ALA PRO FLU SER ARG PRO ALA PRO GLY SER THR ALA PRO PRO ALA HIS GLY VAL THR SER, and
2) ALA PRO ASP THR ARG PRO ALA PRO GLY SER THR ALA PRO PRO ALA HIS GLY VAL THR SER, and
3) ALA PRO GLU THR ARG PRO ALA PRO GLY SER THR ALA PRO PRO ALA HIS GLY VAL SER, and
4) ALA PRO ASP SER ARG PRO ALA PRO GLY SER THR ALA PRO PRO ALA HIS GLY VAL THR SER.

DISCUSSION

It has previously been demonstrated that DF3 antigen in human breast tumors and milk is comprised of mucin-like glycoproteins with molecular weights ranging from 300 to over 450 kd (H. Sekine et al., *J. Immunol* 135, 3610-3615, 1985; M. Abe et al., *J. Cell Physiol.* 126, 126-132, 1986). DF3 antigenicity was found to be sensitive to both neuraminidase and proteases (H. Sekine et al., *J. Immunol* 135, 3610-3615, 1985; M. Abe et al., *J. Cell Physiol.* 126, 126-132, 1986). These results suggested that sialyl oligosaccharides on a peptide backtone are required for DF3 antigenicity. In the present study, MAb DF3 positive plaques were isolated using a lambda gt11 cDNA library prepared from human MCF-7 breast carcinoma cells. The MFC-7 cells have been previously shown to express DF3 antigen (M. Abe et al., *J. Immunol.* 139: 257-261, 1987). One of the positive lambda clones (pDF9.3) was further purified and found to produce a beta-galactosidase fusion protein which specifically reacted with MAb DF3. The reactivity of MAb DF3 with plaques from this expression library and the fusion protein indicates that this antibody reacts with the core protein of DF3 antigen. However, DF3 antigenicity has also been shown to be sensitive to neuraminidase (H. Sekine et al., *J. Immunol* 135, 3510-3615, 1985; M. Abe et al., *J. Cell Physiol.* 126, 126-132, 1986). Thus, MAb DF3 binding to the protein may be enhanced by the presence of glycosidic linkages.

Although patients with breast cancer and certain other carcinomas have higher levels of circulating DF3 antigen, the electrophoretic mobilities of the MAb DF3 reactive species are similar to those in normal subjects (D. Hayes et al., *J. Clin. Invest.* 75, 1671-1678, 1985; H. Sekine et al., *J. Clin. Oncol.* 3: 1355-1363, 1985). Indeed, more recent results have indicated that the variation in electrophoretic mobility of circulating DF3 antigen among family members is related to a genetically determined polymorphism (D. Hayes et al.; *Blood,* 1988, 71:436). The present findings support this genetic polymorphism. Thus, considerable fragment size variation was observed after hybridization of the pDF9.3 probe to EcoRI and PstI restriction digests of DNA from different cell lines. The EcoRI restriction fragments varied from 7 to 12 kb in size and the different cells had only one or two bands. Furthermore, the PstI fragments varied from 3.5 to 6 kb and each DNA preparation similarly yielded one or two bands. In contrast, hybridization of pDF9.3 probe to HindIII DNA digests revealed only one 23 kb band and indicated that this restriction enzyme has digestion sites outside the region identified by this probe.

The variation is allele size identified with pDF9.3 correlated with the presence of different sized transcripts. Thus, cells with two restriction fragments in the EcoRI or PstI DNA digests had two different sized mRNAs. In contrast, BT-20 cells had only one detectable restriction fragment in these DNA digests and expressed only one transcript. This relationship also extended to the variation in electrophoretic mobilities of DF3 antigen. BT-20 cells expressed a single MAb DF3 reactive species, while the other epithelial tumor cells expressed two DF3 antigens. Moreoever, HL-60 cells had no detectable transcripts and no detectable DF3 antigen. Taken together, these findings support out previous findings that the heterogeneity of DF3 antigen production is controlled by multiple alleles at a single locus expressed in an autosomal codominant fashion (D. Hayes et al.; *Blood,* 1987, in press).

The nucleotide sequence analysis of pDF9.3 provides a possible explanation for the variability in restriction fragment size and the polymorphic patterns of DF3 expression. In this regard, we have identified a 309 bp cDNA clone which consists of multiple tandem repeats. These repeats are GC rich and encompass 60 bp. Variation in the size of the DF3 alleles could thus be due to differences in the number of these repeats and occur as a result of unequal crossing-over events. The presence of closely related repeats may also explain the finding that MAb DF3 binds to two or more epitopes in the same DF3 molecules (D. Hayes et al., *J. Clin. Invest.* 75, 1671-1678, 1985). The total number of these repeats in the full length cDNA, however, requires further investigation.

Similar variable tandem repeats have been reported for other genes including those coding for carcinoembryonic antigen (W. Zimmerman et al., *Proc. Natl. Acad. Sci. U.S.A.* 84, 2960-2964, 1987), insulin (Q. I. Bell et al., *Nature* 295: 31-35, 1982), alpha- and beta-globulin (D. R. Higgs et al., *Nucleic Acid Res.* 9, 4213-4224, 1981; R. A. Spritz, *Nucleic Acid Res.* 9, 5037-5047, 1981), Epstein Barr virus (S. H. Speck et al., *Proc. Natl. Acad. Sci. U.S.A.* 83 9298-9310, 1986), c-Ha-ras (D. J. Capon et al., *Nature* 302, 33-37, 1983), and a hypervariable minisatellite family (A. J. Jeffries et al., *Nature* 314: 67-73, 1985). Furthermore, the human complement receptor (CR1) gene consists of homologous repeats approximately 1.6 kb in size (V. M. Holers et al., *Proc. Natl. Acad. Sci. U.S.A.* 84, 2459–2463, 1987). Allelic variants of CR1 differ by 1.6 kb and also correlate with variations in size of both the CR1 transcripts and products (V. M. Holers et al., *Proc. Natl. Acad. Sci. U.S.A.* 84, 2459–2463, 1987). The lengths of most internal repeats, however, range between 120 and 300 bp (W. L. Li in *Evolution of Genes and Proteins,* Eds. M. Nei et al.; Sinaur, Sunderland, Mass. p. 14–37, 1983). Moreover, homology of the internal repeats for many vertebrate proteins ranges between only 20 and 50% (W. L. Li in *Evolution of Genes and Proteins.* Eds. M. Nei et al., Sinaur, Sunderland, Mass., p. 14–37, 1983). In contrast, the internal repeats identified in the present study exhibit a particularly high degree of homology. This finding could suggest that the DF3 gene solved more recently by duplication of a primordial gene or by exon shuffling.

What is claimed is:

1. A polypeptide that:
   (1) is free or substantially free of bound carbohydrate; and
   (2) includes all or a portion of an amino acid sequence that is coded for by a double stranded DNA molecule containing in one strand a first nucleotide sequence

```
CGCACGGCTG GGGGGGCGGT GGAGCCCGGG
GCCGGCCTGC TCTCCGGGGC CGAGGTGACA   60
. CGTG. . . . .  C. . . C. . . . . . . . . . . . . .
. . . . . . . . . . . . . . . . . . . . . . . . . . . . . .  120
. . . . . . . . . . . . . . . . . . . . . . . . . . . . . .
. . . . . . . . . . G . G. . . . . . . . . . . . . . .  180
. . . . . . . . . . G. . . G. . . . . . . . . . . . . .
. . . . . . . . . . . . . . . . . . . . . . . . . . . . . .  240
. . . . . . . . . . . . . . . . . . . . . . . . . . . . . .
. . . . . . . . . . . . . . . . . . . . . . . . . . . . . .  300
. . . . . . . . . .
``` and containing in the other strand a second nucleotide sequence complementary to the first nucleotide sequence.

2. A polypeptide of claim 1 that is free of bound carbohydrate.

3. A polypeptide of claim 2 whose amino acid sequence excludes those amino acid sequences of naturally occurring DF3 antigen that are not included in the amino acid sequence coded for by the human nucleotide sequence depicted in claim 1.

4. A polypeptide of claim 3 that includes all of the amino acid sequence that is coded for by the human nucleotide sequence depicted in claim 1.

5. A polypeptide of claim 1 capable of reacting with anti-DF3 antibody.

6. A polypeptide of claim 1 that was synthesized in a non-human cell.

7. A polypeptide of claim 6 that was synthesized in a prokaryotic cell.

* * * * *

UNITED STATES PATENT AND TRADEMARK OFFICE
CERTIFICATE OF CORRECTION

PATENT NO. : 5,053,489

DATED : Oct. 1, 1991

INVENTOR(S) : Donald W. Kufe

It is certified that error appears in the above—identified patent and that said Letters Patent is hereby corrected as shown below:

Column 2, line 50, "polypeptdie" should read --polypeptide--.
Column 2, line 52, "are" should read --was--.
Column 3, line 9, after "activity" insert --even--.
Column 3, line 32, replace "strucuture" with --structure responsible for the person-to-person variations in DF3 structure--.
Column 3, line 48, "correction" should read --correlation--.
Column 3, line 60 to Column 4, line 3, cancel the following:

```
CGCACGGCTG GGGGGGCGGT GGAGCCCGGG
GCCGGCCTGC TCTCCGGGGC CGAGGTGACA    60
.CGTG..... C...C...........................
............................................  120
..........G..G..............................
..........G...G.............................  180
............................................
............................................  240
............................................
............................................  300
..........
``` and in its place insert the following:

```
CGCACGGCTG GGGGGGCGGT
.CGTG..... C...C.....
.....................
.......... G...G.....
.....................
..........

GGAGCCCGGG        GCCGGCCTGC
   ..........        ..........
   ..........        .........G
   ..........        ..........
   ..........        ..........

TCTCCGGGGC CGAGGTGACA    60
            ..........  ..........   120
            .G........  ..........   180
            ..........  ..........   240
            ..........  ..........   300
```

UNITED STATES PATENT AND TRADEMARK OFFICE
CERTIFICATE OF CORRECTION

PATENT NO. : 5,053,489
DATED : Oct. 1, 1991
INVENTOR(S) : Donald W. Kufe

It is certified that error appears in the above—identified patent and that said Letters Patent is hereby corrected as shown below:

Column 4, line 19, "HIG" should read --HIS--.

Column 4, line 29, "wash" should read --was--.

Column 4, line 60, "GLY" should read --GLU--.

Column 5, line 33, "phosphates" should read --phosphatase--.

Column 5, line 45, "nylong" should read --nylon--.

Column 6, line 10, "phosphates" should read --phosphatase--.

Column 6, line 50, "nylong" should read --nylon--.

Column 8, line 19, "cellulor" should read --cellular--.

Column 9, line 14, "RNA" should read --DNA--.

Column 9, line 26, "FLU" should read --GLU--.

Column 9, line 35, before "SER" add --THR--.

Column 9, line 51, "backtone" should read --backbone--.

Column 10, line 37, "out" should read --our--.

Column 10, line 44, "identificed" should read --identified--.

Column 11, line 19, "solved" should be "evolved".

UNITED STATES PATENT AND TRADEMARK OFFICE
CERTIFICATE OF CORRECTION

PATENT NO. : 5,053,489

DATED : Oct. 1, 1991

INVENTOR(S) : Donald W. Kufe

It is certified that error appears in the above—identified patent and that said Letters Patent is hereby corrected as shown below:

Column 12, lines 1 to 11, cancel the following:

```
CGCACGGCTG GGGGGGCGGT GGAGCCCGGG
GCCGGCCTGC TCTCCGGGGC CGAGGTGACA   60
.CGTG.....  C...C.....  ..........
..........  ..........  ..........  120
..........  ..........  ..........
.........G  .G........  ..........  180
..........  G...G.....  ..........
..........  ..........  ..........  240
..........  ..........  ..........
..........  ..........  ..........  300
..........
``` and insert the following:
--

```
CGCACGGCTG GGGGGGCGGT
.CGTG.....  C...C.....
..........  ..........
..........  G...G.....
..........  ..........
..........

GGAGCCCGGG          GCCGGCCTGC
   ..........          ..........
   ..........          .........G
   ..........          ..........
   ..........          ..........

TCTCCGGGGC CGAGGTGACA   60
              ..........  ..........  120
              .G........  ..........  180
              ..........  ..........  240
              ..........  ..........  300
```

UNITED STATES PATENT AND TRADEMARK OFFICE
CERTIFICATE OF CORRECTION

PATENT NO. : 5,053,489

DATED : Oct. 1, 1991

INVENTOR(S) : Donald W. Kufe

It is certified that error appears in the above-identified patent and that said Letters Patent is hereby corrected as shown below:

(a dot indicating that the nucleotide is identical to the one directly above it in the mode of representation used in this claim)--.

Signed and Sealed this

Third Day of March, 1992

Attest:

HARRY F. MANBECK, JR.

*Attesting Officer*          Commissioner of Patents and Trademarks

UNITED STATES PATENT AND TRADEMARK OFFICE
CERTIFICATE OF CORRECTION

PATENT NO. : 5,053,489
DATED : Oct. 1, 1991
INVENTOR(S) : Donald W. Kufe

It is certified that error appears in the above-indentified patent and that said Letters Patent is hereby corrected as shown below:

In Column 1, between the Title and Background and Overview of the Invention, insert the following:

--Statement of Government Interest

Funding for the present invention was provided in part by the Government of the United States of America by virtue of Grant Nos. CA20531 and CA38879 by the National Institutes of Health. Thus, the Goverment of the United States has certain rights in and to the invention claimed herein. --

Signed and Sealed this

Twentieth Day of May, 1997

*Attest:*

BRUCE LEHMAN

*Attesting Officer*

Commissioner of Patents and Trademarks